Aug. 15, 1967 J. F. SCHMIDT, JR Plant Pat. 2,759

NORWAY MAPLE TREE

Filed Sept. 20, 1965

JOHN FRANK SCHMIDT JR.
INVENTOR

BY
BUCKHORN, BLORE, KLARQUIST & SPARKMAN
ATTORNEYS

United States Patent Office

Plant Pat. 2,759
Patented Aug. 15, 1967

2,759
NORWAY MAPLE TREE

John Frank Schmidt, Jr., 23000 SE. Stark St.,
Troutdale, Oreg. 97060

Filed Sept. 20, 1965, Ser. No. 488,829
1 Claim. (Cl. Plt.—51)

The present invention relates to a new and distinct variety of maple tree, believed to be a variety of the Norway maple, *Acer platanoides*.

The primary distinguishing characteristic of my variety of Norway maple is the form of its leaf which is strikingly more deeply lobed than the leaf of the Norway maple.

My new variety of Norway maple was found by me as a seedling in my nursery which is located near Troutdale, Oreg., and which contains many other trees and particularly Norway maple trees.

I have reproduced in my nursery the new variety, asexually, specifically by removing buds from the parent tree and budding such buds onto regular Norway maple seedlings. After the budding had taken, the upper part of the stock was removed. The characteristics of my tree have proved to be firmly fixed.

Figure 2:
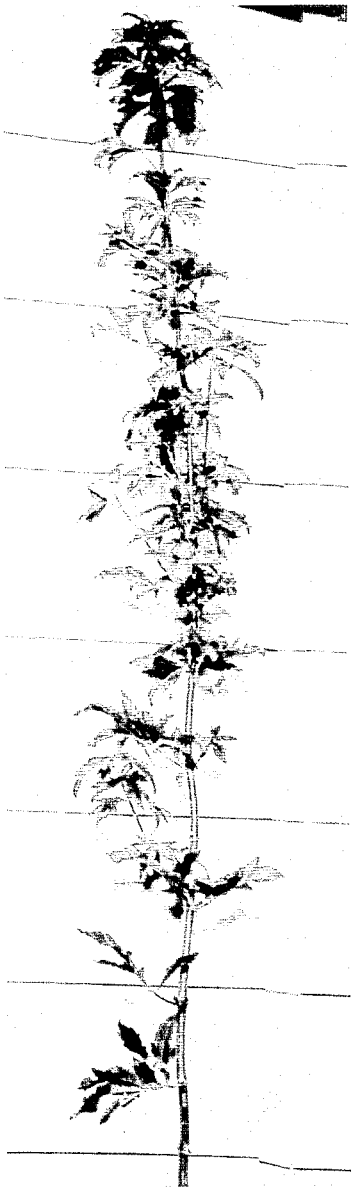
FIG. 2 is a color photograph of a year-old tree of my invention.
Figure 1:
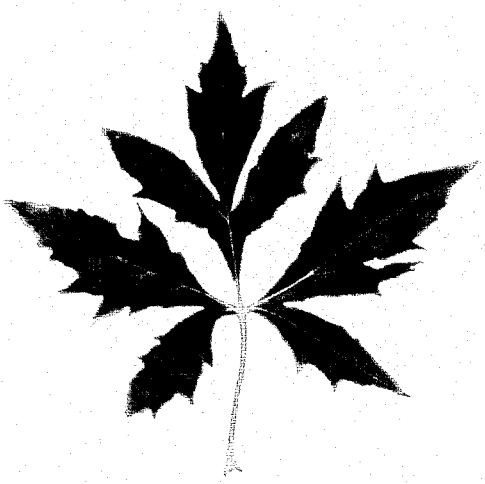
FIG. 1 is a color photograph of a leaf of a tree of my invention, but the colors of the leaf shown are not true, the color in fact being like the leaves in FIG. 2, and more particularly of the color of the leaves of the ordinary Norway maple.

Referring to the drawings and particularly FIG. 1, the leaf shown is generally typical of the leaves of my tree, although it will be appreciated that the leaves of most trees are not of identical form but vary within a range of variations. The variations in the shape of the leaves of my tree are within a range of variation that would be considered as a usual range for maple trees.

Comparing the leaf of FIG. 1, to the leaf of the ordinary Norway maple, it is evident that the blade of the FIG. 1 leaf is much more deeply cleft than that of the ordinary Norway maple leaf so that all the lobes are much better developed than those of the ordinary Norway maple leaf, and particularly the lower two lobes which are distinctly more prominent than the lobes of the ordinary Norway maple. In fact, the clefts or incisions may extend to the midrib as shown in FIG. 1, although in certain leaves the clefts or incisions terminate short of the midrib. Nevertheless, the lobes are so sharply defined that the leaf appears to be of compound rather than simple form. Yet, certain basic features of the ordinary Norway maple leaf are retained and are readily discernible. For instance, the lobes of my leaf are toothed like the lobes of the ordinary Norway maple, although certain of the teeth of my leaf are more fully developed. Still, other of the teeth of my leaf are very similar to the teeth of the ordinary Norway maple in that they have rather wide bases and are short and rather stocky, with the edges thereof closest the respective lobe tips being more abrupt than the opposite edges thereof. Furthermore, the upper edges or margins (as the leaf is depicted in FIG. 1) of the side lobes have either no teeth or teeth of negligible development while the teeth on the lower edges are better defined. This is a characteristic of the ordinary Norway maple leaf. Still further, the leaf of my tree has seven ribs (including the midrib) and thus has seven lobes. The veins of the upper pair of lateral lobes intersect the main vein above the lower common point of intersection of the other lateral lobes with the main vein. This is not so in the case of the leaves of the ordinary *Acer platanoides*.

Insofar as other characteristics of my tree are concerned, they are the same or substantially the same as the ordinary Norway maple, i.e., in regard to size of leaf and tree, color of leaf, color and texture of bark (new growth being a red turning to green), growth habits, etc. In regard to growth habits, my tree during the first year after budding will grow six to eight feet. I have not been able to ascertain the form of the seed since Norway maples do not produce seed until they are approximately ten years old, and my trees are years away from reaching that age. I also point out that the leaf stems of the leaves of my tree contain milky juice which I understand is a characteristic of only the *Acer platanoides* and *Acer macrophyllum* in the maple family.

My tree is distinguishable from other maple trees. For instance, the *Acer platanoides dissectum* is a weakly growing tree and while the leaves are divided, they are deeply laciniately cut which is not so with the leaves of my tree. The *Acer platanoides palmatifidum* has leaves cut to the base but the lobes are deeply laciniated similar to the *dissectum*. The *Acer platanoides laciniatum* has the lobes deeply laciniated, unlike the lobes of my tree. The *Acer platanoides lorbergii* is more like the above three trees than it is like my tree.

Having thus described my invention, I claim:

A new and distinct variety of Norway maple tree substantially as herein shown and described, characterized particularly as to novelty by having leaves more deeply cleft than those of the ordinary Norway maple and with narrower and better developed lobes, particularly better and more prominently developed lower lobes.

No references cited.

ABRAHAM G. STONE, *Primary Examiner.*
ROBERT E. BAGWILL, *Examiner.*